United States Patent [19]

Steer et al.

[11] Patent Number: 4,917,692

[45] Date of Patent: Apr. 17, 1990

[54] FAECAL INCONTINENCE BAG

[75] Inventors: Peter L. Steer; Ronald A. Plass, both of Reigate, England

[73] Assignee: E. R. Squibb and Sons, Inc., Princeton, N.J.

[21] Appl. No.: 45,654

[22] Filed: May 4, 1987

[30] Foreign Application Priority Data

May 9, 1986 [GB] United Kingdom ............... 8611296

[51] Int. Cl.[4] .............................................. A61F 5/44
[52] U.S. Cl. ..................................... 604/355; 604/332
[58] Field of Search ......................... 604/355, 332–345

[56] References Cited

U.S. PATENT DOCUMENTS

| Re. 29,453 | 10/1977 | Weddle | 604/344 |
|---|---|---|---|
| 3,340,540 | 9/1967 | Cella | 604/355 |
| 3,340,876 | 9/1967 | Hill | 128/295 |
| 3,734,096 | 5/1973 | Millebach | 604/355 |
| 3,837,342 | 9/1974 | Mitsuo | 604/344 |
| 3,841,332 | 10/1974 | Treacle | 604/340 |
| 4,185,630 | 1/1980 | Neumeier et al. | 604/344 |
| 4,253,460 | 3/1981 | Chen et al. | 604/344 |
| 4,445,898 | 5/1984 | Jensen | 604/338 |
| 4,490,145 | 12/1984 | Campbell | 604/333 |
| 4,505,976 | 3/1985 | Doehnert | 604/336 |

FOREIGN PATENT DOCUMENTS

| 8500286 | 1/1985 | PCT Int'l Appl. | 604/332 |
|---|---|---|---|
| 2149306 | 6/1985 | United Kingdom | 604/333 |

Primary Examiner—Jerome L. Kruter
Attorney, Agent, or Firm—Donald J. Barrack; Robert E. Lee, Jr.

[57] ABSTRACT

A faecal incontinence bag having flexible front and rear walls secured together around their periphery. The front wall has a hole therein for entry of matter discharged by the wearer. The hole is surrounded by an adhesive pad of skin-compatible water-resistant material secured to the external surface of the front wall surrounding the hole. The pad is generally heart-shaped so that when in position on the wearer the concave portion of the heart-shaped pad is towards the front of the wearer.

10 Claims, 2 Drawing Sheets

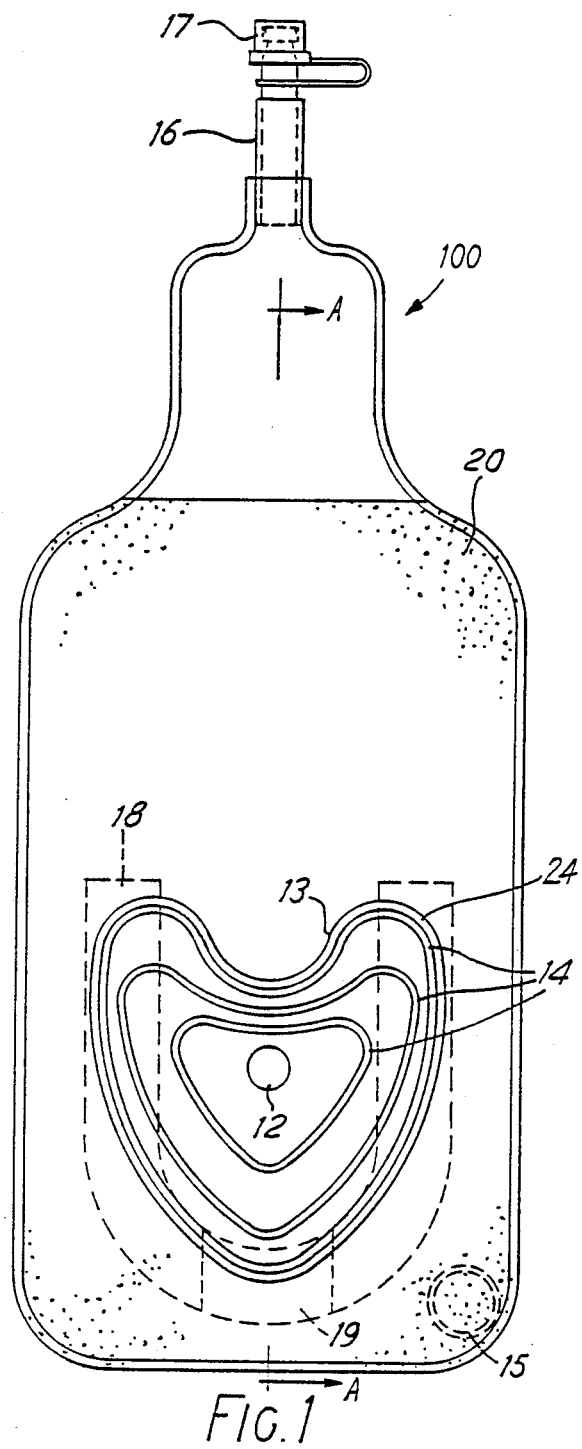
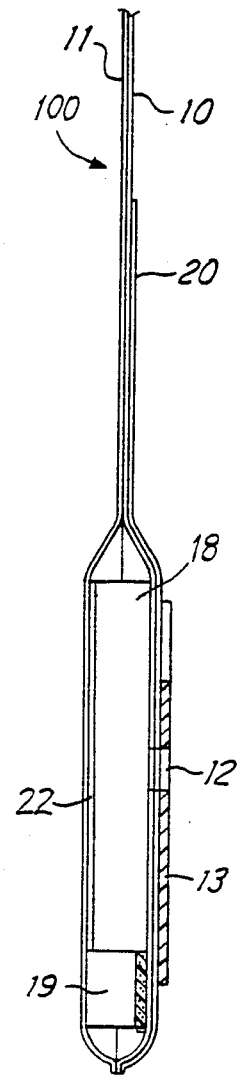
FIG. 1
FIG. 2

FAECAL INCONTINENCE BAG

BACKGROUND OF THE INVENTION

The present invention relates to a bag for receiving waste products for use by persons suffering from faecal incontinence.

Heretofore, faecal incontinence bags have used generally circular adhesive pads for attachment to a subject. In order to provide sufficient support for the bags, the circular pads have had to be relatively large. Such large pads can be difficult to accurately position on the subject to seal around the anus. In addition, large pads are uncomfortable for both male and female subjects in that they may rub against the scrotum in males or interfere with other bodily functions in females.

SUMMARY OF THE INVENTION

According to one aspect of the present invention, there is provided incontinence bag having flexible front and rear walls secured together around their periphery, the front wall having a hole therein for entry of matter discharged by the wearer, the hole being surrounded by an adhesive pad of skin-compatible water-resistant material secured to the external surface of the front wall surrounding the hole, and the pad being of generally heart-shape so that when in position on the wearer the concave portion of the heart-shaped pad is towards the front of the wearer.

According to a further aspect of the invention, there is provided a faecal incontinence bag having flexible front and rear walls secured together around their periphery, the front wall having a hole therein for entry of matter discharged by the wearer, the hole being surrounded by an adhesive pad of skin-compatible water-resistant material secured to the external surface of the front wall surrounding the hole, and at least one resilient pad being provided between the front and rear walls in the region of the hole to urge apart said walls. The adhesive pad is preferably heart-shaped.

The use of a heart-shaped pad in accordance with the invention provides a large area for attachment of the bag to the wearer while being much more comfortable than bags using circular pads. The pad of adhesive is preferably formed from a protective material comprising a blend of a water-soluble or water-swellable hydrocolloid and a water-insoluble viscose elastic binder. One suitable material for the pad is that sold under the trade name "Stomahesive" by E. R. Squibb & Sons. The pad is generally attached to the front wall of the bag by one or more concentric welds and, if desired, the size of the hole can be increased by cutting away material within the area defined by the weld.

The bag may include a filter housing containing gas filtering and deodorizing material in order to allow escape of flatus from the bag. If desired, the bag may also be provided with a drain tube and plug or valve.

The surface of the front wall for contact with the wearer may be provided with a so-called "comfort layer", i.e., a layer of perforated or porous plastic material to prevent the bag from sticking to the wearer.

Bags in accordance with the invention having a resilient pad or cushion between the front and rear walls are generally provided with one such pad of resilient plastic material, e.g., of open cell foam structure. Preferably, the resilient pad is of U-shape, the arms of the U extending along the length of the bag on either side of the hole. In this arrangement, the pad is conveniently provided with a slot at the base of the U so that the bag may be readily folded along its length and inserted between the buttocks of the wearer on attachment. The resilient pad is conveniently secured in place within the bag by gluing or welding to the front and or rear walls.

BRIEF DESCRIPTION OF THE DRAWING

FIG. 1 is a front view of one embodiment of a faecal incontinence bag according to the invention having an optional resilient pad or cushion;

FIG. 2 shows a partial cross section along the line A—A of the bag shown in FIG. 1 including the resilient pad or cushion;

DETAILED DESCRIPTION OF THE PREFERRED EMBODIMENT

Figure 3:
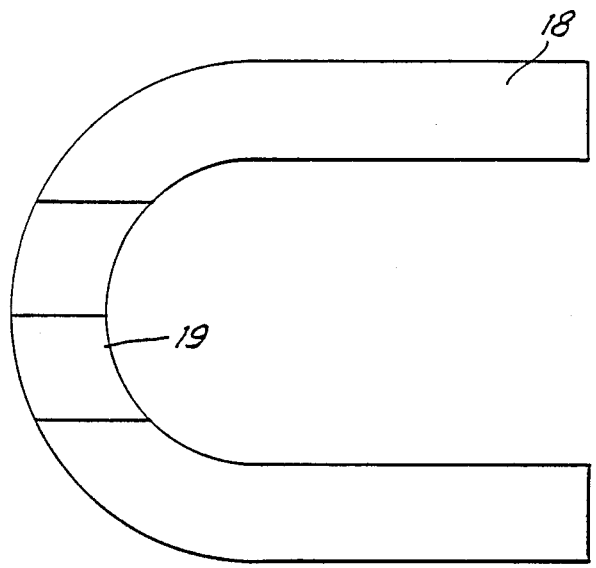
FIG. 3 shows a front view of a resilient pad or cushion for use with a faecal incontinence bag according to the invention.

The faecal incontinence bag 100 shown in FIGS. 1 and 2 has a front wall 10 and a rear wall 11 welded together around their periphery. The front wall 10 has a circular hole 12 therein, and this is surrounded on the external surface of the front wall 10 by a heart-shaped adhesive pad 13 of skin-compatible water resistant material. The pad 13 is secured to the front wall 10 along a series of concentric weld lines 14, and, if desired, the hole 12 may be increased in size for use provided that the outermost weld line 24 is not broken.

Normally, the front and rear walls 10, 11 are made of synthetic plastic material, such as PVC or multilayer films with high odor barrier properties.

A filter housing 15 is located towards the upper end of the rear wall 11. The filter housing 15 incorporates a gas-permeable outer membrane and a hole (not shown) is provided in the rear wall 11 to permit gases from the interior of the bag 100 to pass through the filter.

Figure 4:
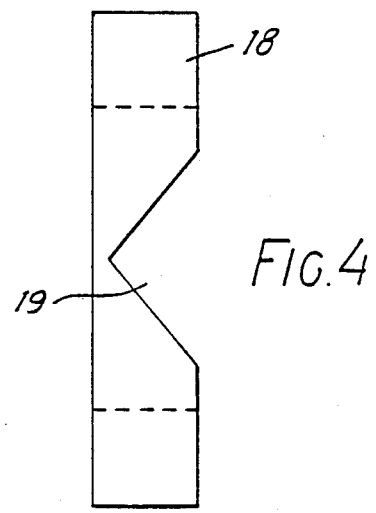
FIG. 4 shows a side view of the resilient pad shown in FIG. 3.

The bag 100 may be provided with an outlet tube 16 together with a suitable closure 17. The faecal incontinence bag 100 according to the invention may also be provided with a resilient pad or cushion 18 which may be glued or welded in position at region 22 to the rear wall 11 which serves to urge the front and rear walls 10, 11 apart. A suitable resilient pad 18 is shown in FIGS. 3 and 4. The resilient pad 18 shown is generally U-shaped, but it will be appreciated that other shapes may be used. The pad 18 shown is approximately 15 mm thick and is provided with a V-shaped cut away 19 to enable the pad 18 to be readily folded along its length. The resilient pad is conveniently formed from a closed cell plastic, e.g. low density polyethylene/EVA.

The faecal incontinence bag 100 according to the invention is conveniently provided with a layer of perforated or porous plastic 20 on the front panel. This layer helps to improve comfort for the wearer.

In use, the bag 100 may be folded along its length with the front wall 10 facing outwards. The folded bag 100 may then be introduced between the buttocks of the subject so that the hole 12 aligns with the anus of the subject and with the concave side of the heart-shaped adhesive pad 13 having holes which form the concave portion facing towards the front of the subject. The adhesive pad 13 is then sealed against the skin of the subject. Both the shape of the adhesive pad 13 and the provision of the resilient pad 18 help to attach the bag 100 to the subject. In addition, the shape of the adhesive pad 13 provides for comfortable wear by the subject. The provision of the resilient pad 18 also improves comfort for the subject particularly when the bag 100 contains waste material.

I claim:

1. A faecal incontinence bag having flexible front and rear walls secured together around their periphery, the front wall having a hole therein for entry of matter discharged by the wearer, the hole being surrounded by an adhesive pad of skincompatible water-resistant material secured to the external surface of the front wall surrounding the hole, and the pad being generally of heart-shape which is symmetric about a longitudinal axis and comprises a concave portion substantially bisected at one end of said axis having holes forming said concave portion and a generally convex portion bisected at the opposite end of said axis so that when in position on the wearer the holes of the concave portion of the heart-shaped pad is towards the front of the wearer.

2. The faecal incontinence bag of claim 1 in which the pad of adhesive is formed from a protective material comprising a blend of a water-soluble or water-swellable hydrocolloid and a water-insoluble viscose elastic binder.

3. The faecal incontinence bag of claim 1 in which the adhesive pad is attached to the front wall of the bag by one or more concentric welds.

4. The faecal incontinence bag of claim 1 including a filter housing containing gas filtering and deodorizing material in order to allow escape of flatus from the bag.

5. The faecal incontinence bag of claim 1 including a drain tube and plug or valve.

6. The faecal incontinence bag of claim 1 in which the surface of the front wall for contact with the wearer is provided with a layer of perforated or porous plastic material to prevent the bag from sticking to the wearer.

7. The incontinence bag of claim 1 wherein said bag further comprises at least one resilient pad being provided between the front and rear walls in the region of the hole to urge apart said walls.

8. The faecal incontinence bag of claim 7 in which the resilient pad is of U-shape, the arms of the U extending along the length of the bag on either side of the hole.

9. The faecal incontinence bag of claim 8 in which the resilient pad is provided with a slot at the base of the U so that the bag may be readily folded along its length and inserted between the buttocks of the wearer on attachment.

10. The faecal incontinence bag of claim 9 in which the resilient pad is of resilient plastics open cell foam material.

* * * * *